(12) United States Patent
Burkhart et al.

(10) Patent No.: US 6,524,602 B1
(45) Date of Patent: Feb. 25, 2003

(54) POLYMER DELIVERY SYSTEM IN TREATMENTS FOR PARASITIC SKIN DISEASES

(76) Inventors: Craig G. Burkhart, 4556 Crossfields Rd., Toledo, OH (US) 43623; Craig N. Burkhart, 4556 Crossfields Rd., Toledo, OH (US) 43623

( * ) Notice: Subject to any disclaimer, the term of this patent is extended or adjusted under 35 U.S.C. 154(b) by 0 days.

(21) Appl. No.: 09/986,209

(22) Filed: Oct. 22, 2001

Related U.S. Application Data

(63) Continuation-in-part of application No. 09/416,782, filed on Oct. 13, 1999.
(60) Provisional application No. 60/104,089, filed on Oct. 13, 1998, and provisional application No. 60/109,826, filed on Nov. 25, 1998.

(51) Int. Cl.⁷ .............................................. A61K 31/40
(52) U.S. Cl. ........................ 424/405; 514/30; 424/427
(58) Field of Search ................................ 424/405, 407; 514/30

(56) References Cited

U.S. PATENT DOCUMENTS

| | | | | |
|---|---|---|---|---|
| 5,411,737 A | * | 5/1995 | Hsu et al. | |
| 5,516,761 A | * | 5/1996 | Choi et al. | |
| 5,696,158 A | * | 12/1997 | Oliver | |
| 5,814,325 A | * | 9/1998 | Rod | |
| 5,837,228 A | * | 11/1998 | Shih et al. | |
| 6,258,369 B1 | * | 7/2001 | Pullen | |

* cited by examiner

*Primary Examiner*—William R. A. Jarvis
*Assistant Examiner*—Vickie Kim
(74) *Attorney, Agent, or Firm*—MacMillan, Sobanski & Todd, LLC

(57) ABSTRACT

A formulation for the treatment of a parasitic skin disease includes a parasiticide to kill the parasite. The formulation also includes a polymer effective to increase retention of the formulation on the skin, and to reduce absorption of the formulation into the skin. Alternatively, the formulation may include a polymer such as a beta-sheet breaker peptide which is effective to increase absorption of the insecticide into the head lice and/or the eggs of the head lice. The formulation also includes a vehicle for the polymer and the parasiticide.

1 Claim, No Drawings

POLYMER DELIVERY SYSTEM IN TREATMENTS FOR PARASITIC SKIN DISEASES

CROSS-REFERENCE TO RELATED APPLICATIONS

This application claims the benefit of provisional application No. 60/104,089, filed Oct. 13, 1998 and Ser. No. 60/109,826, filed Nov. 25, 1998, and this application is a continuation-in-part of Ser. No. 09/416,782, filed Oct. 13, 1999.

FIELD OF INVENTION

This invention relates to treatments for parasitic skin diseases such as infestations with lice or mites, and in particular to improved treatments for such diseases that contain a polymer delivery system.

BACKGROUND OF THE INVENTION

Parasitic skin diseases, such as infestations with lice or mites, cause much suffering in both humans and animals. For example, head lice is a persistent problem, especially among elementary school-aged children. It was reported that six million U.S. school children will become infested with head lice in one year, that is one out of every four students in elementary schools (*Consumer Reports*, February 1998). The total number of people in the U.S. infested with head lice in one year is about ten million when all ages are accounted for. The incidence of head lice is only slightly improved from the reported incidence in 1940, which was prior to the advent of insecticides and "superior" knowledge by the medical establishment.

Infestation with head lice typically causes itching of the scalp. In some cases, a person may develop lesions or papules on the scalp, swollen glands in the neck or under the arms, or other symptoms. A secondary problem is that many schools have enforced absenteeism if a child has any nits (lice eggs) in their hair. Such a "no-nit" policy has negative social implications for the child and parents. Head lice is becoming a sensitive social issue.

Although head lice are not generally considered to be vectors for systemic human infection, the evidence strongly supports the possibility that head lice could be vectors. For example, rickettsiae and spirochetes are known to be obtainable from the blood of the host (head lice are blood suckers like mosquitoes); these organisms multiply in the gut of the head lice, and are also found in high numbers in their feces. Viruses, like the AIDS virus, also can be found in the gut and feces of head lice, but these organisms do not multiply in the gut of the louse; thus, the number of viruses in the feces would not be high. However, any organism in the blood of the host would be found in the feces of the louse, and thereby, could be potentially transmitted when the louse finds a new host, i.e., a new human being to infest.

Various over-the-counter and prescription topical treatments for head lice are currently available. These treatments are no longer as effective as in previous years in killing adult head lice and nits. In fact, an article in the September, 1999 issue of Archives of Pediatrics and Adolescent Medicine reported that only 90% of adult head lice are killed by the two main products currently used in head lice therapy, Nix and Rid. It is clear that resistance or tolerance of head lice to insecticides has increased in recent years. The reduced effectiveness of current treatments raises the possibility that people may resort to the use of dangerous agents such as kerosene to treat head lice, or may resort to the use more toxic insecticides that could damage the scalp. Thus, it would be desirable to provide a more effective treatment for head lice and other parasitic skin diseases that avoids the need to use such drastic measures, particularly since the majority of head lice patients are children.

Various polymers are presently being used in medicine. TopiCare by Penederm and Berteck Laboratory is a polyol-prepolymer included in "Avita", a topical skin cream with vitamin A. Ortho Division of Johnson and Johnson produces "Retin A Micro", a skin product containing vitamin A in a microsponge polymer made by Advanced Polymer Systems. Additionally, Chitogenics makes a polymer called N,O-carboxymethylchitosan (NOCC), a glycosaminoglycan synthesized from the natural polysaccharide, chitin. NOCC and other polymers have been proven to be of value in drug delivery, preventing post-surgical adhesions, wound management, and arthoscopic surgical aids. In Japan, polymers are used as flocculents in the clarification of waste water and beverages, in food processing, and in moisturizers that adhere well to skin and hair. In particular, chitosan polymers are used in many skin creams and hair care products in Japan. However, it has never been suggested to use a polymer delivery system in improved treatments for parasitic skin diseases.

SUMMARY OF THE INVENTION

This invention relates to a formulation for the treatment of a parasitic skin disease. In a preferred embodiment, the formulation is effective for the treatment of head lice. The formulation includes a parasiticide to kill the parasite. The formulation also includes a polymer effective to increase retention of the formulation on the skin, and to reduce absorption of the formulation into the skin. The formulation also includes a vehicle for the polymer and the parasiticide.

In another embodiment for the treatment of head lice, the formulation includes an insecticide and a polymer such as a beta-sheet breaker peptide which is effective to increase absorption of the insecticide into the head lice and/or the eggs of the head lice.

Various objects and advantages of this invention will become apparent to those skilled in the art from the following detailed description of the preferred embodiments.

DETAILED DESCRIPTION AND PREFERRED EMBODIMENTS OF THE INVENTION

The present invention relates to the use of a polymer delivery system in treatments for parasitic skin diseases, to provide improved therapeutics and to reduce potential hazards of the treatments. The parasitic skin diseases to be treated include any diseases in which parasites infest the surface of the skin, especially on those skin areas covered by hair, such as the scalp and pubic area. Such diseases include, for example, infestations with lice, especially head lice and pubic lice, and mites (e.g., scabies, chiggers, Demodex mites, and the like).

The polymer delivery system is effective to increase retention of the formulation on the outside surface of the skin, and to reduce absorption of the formulation into the skin. In a treatment for head lice, the polymer increases the retention of the treatment on the hair and the outside surface of the scalp, and reduces the absorption of the treatment into the skin. As a result, the polymer delivery system provides one or more of the following advantages. The polymer delivery system can allow the use of higher concentrations of parasiticide on the skin without risk of increased toxicity.

The polymer delivery system can also allow parasiticides to stay on the skin for longer time periods without risk of increased toxicity. Additionally, the polymer delivery system can allow the use of parasiticides that are sometimes considered too toxic to be used, because the parasiticides are not significantly absorbed into the skin and are therefore measurably less toxic. There is a great demand for such a treatment in therapies for parasitic skin diseases.

Given the increasing resistance of head lice to various insecticides, the polymer delivery system will allow over-the-counter and prescription topical products to add efficacy by keeping the insecticide on the hair and skin surface for a longer period of time, while reducing absorption of the insecticide into the skin and thereby reducing the risk of toxicity. This is applicable because head lice normally shut down absorption by closing off their spiracles (respiratory channels). These channels are the method by which head lice obtain oxygen as they have no lungs. Head lice can shut down these spiracles for over an hour without ill effects, but by allowing insecticide products more time of exposure to the head lice, the formulations of the invention will allow more penetration when the head lice reopen their spiracles. More prolonged application by means of the polymer delivery system should also result in better penetration into the nit which is lipophilic with several membranes to penetrate before getting to the developing egg. Typically, the formulation is retained on the scalp for either about 10 minutes or overnight (e.g., about 7–9 hours), depending on the particular patient.

In the case of over-the-counter head lice products containing pyrethrum extract, the polymer deliver system increases efficacy by at least partially overcoming resistance of the head lice to the insecticide, while reducing absorption of the insecticide into the skin to reduce potential toxicity. In the case of prescription head lice products such as malathion (Ovide by Medicis, which is presently sold in a 78% alcohol base), the insecticide could be formulated in a polymer base initially, or the existing product could be incorporated into a final polymer formulation. This would not only increase the efficacy of the product, but would also decrease its flammability (which is definitely a concern with this particular product in this childhood disease).

In addition to the above-mentioned advantages, the polymer will aid in louse and nit removal when the formulation is used to treat head lice. The polymer also decreases the egg laying ability of the louse, by decreasing the attachment of the eggs.

The parasiticides useful in the treatments include any materials effective for killing the parasites, such as various insecticides. Some insecticides that may be used include, but are not limited to, permethrin, pyrethrin (in higher concentrations than presently allowed), gamma benzene hexachloride, malathion, ivermectin, moxidectin, other macrocyclic lactones such as compound F28249, doramectin, pyrantel pamoate, fenbendaxole, oxibendazole, benzimidazole, thiabendazole, abamectin, avermectin, carboxyl, DDT (chlorophenothene), cromiton, benzylbenzoate, temephos, coumaphos, diazinon, sumithrine, fluorescein, pyrantel embonate, carbophenothiion, chlorfenvinphos, crotoxyphos, fenitrothioin, derris, bromocyclen, diflubenzuron, organophosphates, organochlorines, nicotine, hexachlorocyclohexanes, crotoxyphos (plus dichlorvos), stirofos, tetrachlorvinphos, adioxathion, phosmet, bromocyclen, famphur, fenthion, methoxychlor, totoqhene, trichlorfon, cypermethrin, bioallethrin, cyano substituted pyrethroid, phenothrin, pirimiphos methyl, carbaryl, propoxur, temepho, pralidoxine, parathion, and natural insecticidal oils such as coconut oil, anise, ylang ylang, garlic, and lavender. The amount of insecticide in the formulation is usually within a range of from about 0.25% to about 10% by weight of the formulation.

The polymer delivery system can be any polymer, or combination of polymers, capable of better retaining the treatment on the surface of the skin and reducing absorption into the skin. The polymer(s) of the polymer delivery system can be water soluble, or non-water soluble, and can come in various lengths to accommodate one's needs. Some polymers can change from a solution state to solid state dependent upon temperature. Thus, a polymer could be in solid form at room temperature, but in a solution state when heated a few degrees more. The amount of polymer in the formulation is usually within a range of from about 0.5% to about 20% by weight of the formulation.

Preferred polymers for use in the polymer delivery system include, but are not limited to, microsponge polymers, polytrap polymers, N,O-carboxymethyl-chitosan ("NOCC"), polyolprepolymers, chitosan polymers, and beta-sheet breaker peptides. Microsponge polymers consist of polymeric beads having a network of pores. One such microsponge polymer is available commercially from Advanced Polymer Systems, Redwood City, Calif. The microsponge polymer is described in more detail in U.S. Pat. No. 4,690,825 to Won, issued Sep. 1, 1987, and in U.S. Pat. No. 5,145,675 to Won, issued Sep. 8, 1992 (both of which are incorporated by reference herein).

Polytrap polymers are highly cross-linked polymethacrylate copolymers. Such a polymer is manufactured by Dow Corning Corporation, Midland, Mich., and sold under the trademark Polytrap. It is powder having particles capable of absorbing high levels of lipophilic liquids and some hydrophilic liquids. The powder structure consists of a lattice of unit particles less than one micron that are fused into agglomerates of 20 to 100 microns, and the agglomerates are loosely clustered into macro-particles or aggregates of about 200 to about 1200 micron size. Advanced Polymer Systems also sells a Polytrap System which can be used in the invention.

NOCC is a chitosan derivative having carboxymethyl substituents on some of both the amino and primary hydroxyl sites of the glucosamine units of the chitosan structure. One such polymer is available commercially from Chitogenics, Inc., Halifax, Nova Scotia, Canada. This polymer is described in detail in U.S. Pat. No. 4,619,995 to Hayes, issued Oct. 28, 1986, U.S. Pat. No. 5,679,658 to Elson, issued Oct. 21, 1997, and U.S. Pat. No. 5,888,988 to Elson, issued Mar. 30, 1999 (all of which are incorporated by reference herein).

Polyolprepolymer is a mixture of liquid hydroxyl terminated polymers and polyethylene glycol. One such polymer, Polyolprepolymer-2, is available commercially from Bamet Products, Inc., Englewood Cliffs, N.J.

Chitosan is deacetylated chitin, or poly-N-acetyl-D-glucosamine. It is available commercially from many sources, such as Protan Laboratories Inc., Redmond, Wash. As used herein, "chitosan" includes chitosan, inorganic or organic salts of chitosan, and any chemically modified forms of chitosan or chitosan derivatives. This polymer is described in detail in U.S. Pat. No. 5,141,964 to Noel, issued Aug. 25, 1992, and U.S. Pat. No. 5,744,166 to Illum, issued Apr. 28, 1998 (both of which are incorporated by reference herein).

Certain polypeptides such as beta-sheet breaker peptides are another type of polymer that is preferred for use in the invention. The beta-sheet breaker peptides would be used to loosen the nit sheath and any other louse parts affected by the polymer, instead of increasing retention of the formulation on the skin or reducing absorption of the formulation into the skin. This beta-sheet breaker peptides may increase absorption of insecticides into the egg or louse.

It should be understood that the above-mentioned polymer examples are not intended to be limiting, and that numerous other types of polymers can be used in the formulations of the invention.

The formulations also include a vehicle or carrier for the polymer and the parasiticide. Typically, the carrier is water. The polymer and the parasiticide are usually dispersed in the carrier. The carrier can also include an alcohol such as isopropyl alcohol, propylene glycol and/or polyethylene glycol.

The formulations may also include other categories of materials to improve the effectiveness of the formulations. For example, the formulations may include one or more of the following agents:

- an agent that would affect the bacterial symbiotes which live in the guts of the head lice.
- an agent that affects the beta-sheathing of the nit sheath. The beta-sheathing is the type of protein binding that makes the nit sheath solidify on exposure to air.
- a chitinolytic agent. Chitin is the external skeleton of the louse, and such an agent may have various effects such as affecting their joints so that they cannot squat to lay eggs, or may affect their ability to keep moisture in their bodies.
- an agent that affects the respiratory system of the head lice (such as irritating their spiracles or increasing the $CO_2$ so that they are not properly oxygenated).
- an agent that affects the muscle tone of the head lice (so that they would not be able to cling to hair very well).
- an antimetabolite, or agent that affects the nutrition of the head lice. These will affect their survival if given for prolonged intervals in a hair gel.
- an agent that is hormonal. Such an agent would mostly affect the instars, the developing adults.
- an agent that affects the sensory perception of the head lice. These insects are very smell sensitive and this could affect their behavior considerably.
- an agent that dries out the head lice. These insects dry out easily when off the human scalp. Indeed, that is what they die of when they fall off the scalp hair.
- an agent that affects oviposition (anything that deters the female from squatting and laying eggs).

The formulations may optionally include ingredients for enhancing the consistency and feel of the formulations, for example, a fatty acid such as oleic acid. Other optional ingredients include an antioxidant such as tocopherol, a preservative such as methylparaben or propylparaben, glycerine, and sorbitol.

The formulations can be prepared in any suitable manner, so long as the polymer and parasiticide are well mixed so that the polymer is effective to increase retention of the parasiticide on the skin and to reduce absorption of the parasiticide into the skin. Typically, the ingredients are mixed together until the ingredients are well dispersed throughout the formulation. In a preferred embodiment, the parasiticide is mixed initially with a polymer base so that it is incorporated into the base, and then the polymer base with incorporated parasiticide is mixed with the remaining ingredients of the formulation.

The following examples describe specific preferred formulations for treating head lice that could be made in accordance with the invention:

EXAMPLE 1

0.25–0.5% (by weight) insecticide
0.5–10% polymer base (NOCC)
0–5% oleic acid
0–25% propylene glycol
water (remainder)

EXAMPLE 2

0.25–0.5% (by weight) insecticide
0.5–10% polymer base (NOCC)
25–78% isopropyl alcohol
0–40% propylene glycol
0–5% oleic acid
water (remainder)

EXAMPLE 3

0.25–0.5% (by weight) malathion
2–5% polymer base (NOCC)
25–75% isopropyl alcohol
0–50% polyethylene glycol
0–5% oleic acid
water (remainder)

The principle and mode of operation of this invention have been described in its preferred embodiments. However, it should be noted that this invention may be practiced otherwise than as specifically described without departing from its scope.

What is claimed is:

1. A formulation for the treatment of a parasitic skin disease consisting essentially of:

a parasiticide;

a N,O-carboxymethyl-chitosan polymer effective to increase retention of the formulation on the skin and to reduce absorption of the formulation into the skin; and a vehicle for the polymer and the parasiticide.

* * * * *